(12) United States Patent
Batarseh et al.

(10) Patent No.: US 9,939,421 B2
(45) Date of Patent: Apr. 10, 2018

(54) EVALUATING EFFECTIVENESS OF CERAMIC MATERIALS FOR HYDROCARBONS RECOVERY

(71) Applicant: Saudi Arabian Oil Company, Dhahran (SA)

(72) Inventors: Sameeh Batarseh, Dhahran (SA); Hazim Hussein Abass, Dhahran (SA); Ayman Raja Al-Nakhli, Dammam (SA)

(73) Assignee: Saudi Arabian Oil Company, Dhahran (SA)

(*) Notice: Subject to any disclaimer, the term of this patent is extended or adjusted under 35 U.S.C. 154(b) by 543 days.

(21) Appl. No.: 14/482,679

(22) Filed: Sep. 10, 2014

(65) Prior Publication Data

US 2016/0069857 A1 Mar. 10, 2016

(51) Int. Cl.
*E21B 43/24* (2006.01)
*G01N 33/38* (2006.01)
*G01N 33/24* (2006.01)
*G01N 33/28* (2006.01)

(52) U.S. Cl.
CPC ........ *G01N 33/388* (2013.01); *E21B 43/24* (2013.01); *G01N 33/24* (2013.01); *G01N 33/28* (2013.01)

(58) Field of Classification Search
None
See application file for complete search history.

(56) References Cited

U.S. PATENT DOCUMENTS

| 4,019,575 A | * | 4/1977 | Pisio | ............ E21B 43/24 166/302 |
| 4,185,691 A | | 1/1980 | Tubin et al. | |
| 4,437,519 A | * | 3/1984 | Cha | ............ C10L 1/04 137/13 |
| 4,620,593 A | | 11/1986 | Haagensen | |

(Continued)

FOREIGN PATENT DOCUMENTS

| WO | WO2011101739 | 8/2011 |
| WO | WO 2012038814 | 3/2012 |

OTHER PUBLICATIONS

Li, Kewen, et al. "Application of carbon nanocatalysts in upgrading heavy crude oil assisted with microwave heating." Nano letters 14.6 (2014): 3002-3008.*

(Continued)

*Primary Examiner* — Peter Macchiarolo
*Assistant Examiner* — Herbert K Roberts
(74) *Attorney, Agent, or Firm* — Fish & Richardson P.C.

(57) ABSTRACT

Example methods and systems are described for evaluating an effectiveness of ceramic particles to recover heavy oil from a subterranean region. In some aspects, a heavy oil recovery evaluation system includes a vessel containing a mixture of heavy oil and sand, the vessel including a chamber to receive a plurality of ceramic particles and water, a probe connected to the vessel to transfer energy from an energy source for energizing the plurality of ceramic particles, wherein the energized ceramic particles convert the water into steam to recover the heavy oil from the mixture, and a computer system connected to the vessel to evaluate an effectiveness of the plurality of ceramic particles to recover heavy oil from the mixture.

26 Claims, 3 Drawing Sheets

(56) References Cited

U.S. PATENT DOCUMENTS

| | | | |
|---|---|---|---|
| 5,367,157 A * | 11/1994 | Nilsson | B04B 5/02 250/231.13 |
| 5,623,576 A | 4/1997 | Deans | |
| 5,899,274 A | 5/1999 | Frauenfeld et al. | |
| 6,285,014 B1 | 9/2001 | Beck et al. | |
| 6,332,500 B1 * | 12/2001 | Ellefsen | B63B 21/50 114/230.2 |
| 6,387,327 B1 * | 5/2002 | Ricci | B04B 5/0414 422/561 |
| 6,405,802 B1 * | 6/2002 | Williams | E21B 41/10 166/338 |
| 6,544,411 B2 | 4/2003 | Varadarah | |
| 6,814,141 B2 | 11/2004 | Huh et al. | |
| 6,932,155 B2 * | 8/2005 | Vinegar | B09C 1/02 166/245 |
| 7,091,460 B2 | 8/2006 | Kinzer | |
| 7,828,057 B2 | 11/2010 | Kearl et al. | |
| 8,378,275 B2 | 2/2013 | Novak | |
| 8,485,254 B2 | 7/2013 | Huber et al. | |
| 8,555,969 B2 | 10/2013 | Goodwin et al. | |
| 2003/0173072 A1 * | 9/2003 | Vinegar | B09C 1/02 166/66.5 |
| 2005/0207938 A1 * | 9/2005 | Hanawa | G01N 35/1002 422/64 |
| 2007/0131594 A1 | 6/2007 | Hakola | |
| 2007/0267191 A1 * | 11/2007 | Pfeiffer | E21B 33/138 166/252.5 |
| 2007/0284107 A1 * | 12/2007 | Crichlow | E21B 43/166 166/302 |
| 2007/0289736 A1 | 12/2007 | Kearl et al. | |
| 2009/0008079 A1 * | 1/2009 | Zazovsky | E21B 36/04 166/60 |
| 2009/0252842 A1 * | 10/2009 | Wang | A23L 3/32 426/231 |
| 2010/0089584 A1 * | 4/2010 | Burns | E21B 43/2401 166/302 |
| 2010/0095742 A1 | 4/2010 | Symington et al. | |
| 2012/0000642 A1 * | 1/2012 | Betzer Tsilevich | B03D 1/02 166/57 |
| 2012/0048118 A1 * | 3/2012 | Hess | B01D 17/02 96/183 |
| 2014/0050619 A1 * | 2/2014 | Meller | B01L 3/5082 422/63 |
| 2014/0110118 A1 * | 4/2014 | Hocking | E21B 43/26 166/305.1 |
| 2017/0097305 A1 * | 4/2017 | Prinz | G01N 21/9027 |

OTHER PUBLICATIONS

Al-Nakhli et al., "Enhanced Oil Recovery by In-Situ Steam Generation", U.S. Appl. No. 61/652,359, filed Jun. 7, 2010, 25 pages.
Sameeh Issa Batarseh, "Electromagnetic Assisted Ceramic Materials for Heavy Oil Recovery and In-Situ Steam Generation", U.S. Appl. No. 14/147,914, filed Jan. 6, 2014, 18 pages.
Sameeh Issa Batarseh, "Electromagnetic Assisted Ceramic Materials for Heavy Oil Recovery and In-Situ Steam Generation", U.S. Appl. No. 14/148,075, filed Jan. 6, 2014, 17 pages.
International Search Report and Written Opinion of the International Searching Authority issued in International Application No. PCT/US2015/047412 dated Oct. 30, 2015; 12 pages.
Bientinesi, Matteo et al.; "A New Technique for Heavy Oil Recovery Based on Electromagnetic Heating: Pilot Scale Experimental Validation"; Chemical Engineering Transactions, vol. 32; Jun. 2, 2013; pp. 2287-2292.
Berkowitz, N. et al.; "Extraction of Oil Sand Bitumens with Supercritcal Water"; Fuel Processing Technology, 25, No. 1; Apr. 1, 1990; pp. 33-44.
Cerutti, Alessandro, et al.; "A New Technique for Heavy Oil Recovery Based on Electromagnetic Heating: System Design and Numerical Modelling"; Chemical Engineering Transaction, vol. 32; Dec. 31, 2013; pp. 1255-1260.

* cited by examiner

EVALUATING EFFECTIVENESS OF CERAMIC MATERIALS FOR HYDROCARBONS RECOVERY

TECHNICAL FIELD

This disclosure relates to evaluating effectiveness of ceramic materials to recover hydrocarbons from a subterranean region (e.g., a region from which heavy viscous oil or other hydrocarbons can be extracted, or other types of regions).

BACKGROUND

Hydrocarbon recovery is a process that by which hydrocarbon are extracted from a subterranean region. Hydrocarbon recovery can include primary recovery and secondary recovery. Primary recovery relies on natural pressure of the hydrocarbons in the subterranean region which allows extracting them without any effort. Once the pressure of the formation decreases, secondary recovery techniques can be employed to further extract hydrocarbons from the subterranean region.

Secondary recovery techniques rely on a supply of external energy into the subterranean region to drive the hydrocarbons to flow from a targeted formation into a well bore for production. In many instances, thermal energy is introduced to the formation, for example, by steam injection or in-situ combustion, to lower the viscosity and enhance the production of the hydrocarbons from the formation.

SUMMARY

This disclosure describes systems and methods for evaluating effectiveness of ceramic materials to recover hydrocarbons from a subterranean region.

In general, example innovative aspects of the subject matter described here can be implemented as a heavy oil recovery evaluation system. The heavy oil recovery evaluation system can include a vessel containing a mixture of heavy oil and sand, the vessel including a chamber to receive multiple ceramic particles and water, a probe connected to the vessel to transfer energy from an energy source for energizing the ceramic particles, wherein the energized ceramic particles convert the water into steam to recover the heavy oil from the mixture, and a computer system connected to the vessel to evaluate an effectiveness of the ceramic particles to recover heavy oil from the mixture.

This, and other aspects, can include one or more of the following features. The probe is configured to transfer at least one of microwave energy, radio frequency energy, electrical energy, or laser energy to heat the ceramic particles.

In some aspects, the vessel is a first vessel, and wherein the system further includes a second vessel positioned in the chamber, wherein the ceramic particles and the water are received in the second vessel. In some instances, the second vessel includes a mesh to permit the steam to pass through.

In some aspects, the heavy oil recovery evaluation system further includes multiple sensors connected to the computer system to measure properties of one or more of the heavy oil, the ceramic particles, or the steam. The sensors can include one or more of a temperature sensor to measure a temperature of the steam, a pressure sensor to measure a pressure of the steam, or a viscometer to measure a viscosity of the heavy oil.

In some aspects, to evaluate an effectiveness of the ceramic particles to recover heavy oil from the mixture, the computer system is configured to obtain the measured properties of the one or more of the heavy oil, the ceramic particles, or the steam, and to evaluate the effectiveness of the ceramic particles to recover heavy oil from the mixture based on the measured properties.

In some aspects, the heavy oil recovery evaluation system includes a swivel connected to the vessel to swivel the vessel. In some instances, an axis of the vessel is substantially vertical and wherein the probe is inserted into the vessel horizontally or at an angle to the axis.

Another innovative aspect of the subject matter described here can be implemented as a method. A mixture of heavy oil and sand is placed into a vessel including a chamber. Multiple ceramic particles are placed into the chamber. The ceramic particles are energized using a probe connected to the vessel. Water is added into the chamber. The energized ceramic particles are allowed to convert the water into steam to recover the heavy oil from the mixture. An effectiveness of the ceramic particles to recover heavy oil from the mixture is evaluated.

This, and other aspects, can include one or more of the following features. Energizing ceramic particles using a probe connected to the vessel can include heating the ceramic particles using a probe transferring at least one of microwave energy, radio frequency energy, electrical energy, or laser energy.

In some aspects, properties of one or more of the heavy oil, the ceramic particles, or the steam are measured. In some instances, the recovered heavy oil is collected and a property of the recovered heavy oil is measured.

In some aspects, evaluating an effectiveness of the ceramic particles to recover heavy oil from the mixture can include obtaining the measured properties of the one or more of the heavy oil, the ceramic particles, or the steam, and evaluating the effectiveness of the ceramic particles to recover heavy oil from the mixture based on the measured properties.

A further innovative aspect of the subject matter described here can be implemented as a method. Ceramic particles are energized using energy from two or more energy sources. The ceramic particles are positioned in a chamber in a vessel that includes a mixture of heavy oil and sand. Heavy oil is recovered from the mixture using steam formed by flowing water over the energized ceramic particles. An effectiveness of the ceramic particles to recover heavy oil from a subterranean region is evaluated based, at least in part, on a property of the heavy oil recovered from the mixture This, and other aspects, can include one or more of the following features. The energy sources can include two or more of a microwave energy source, a radio frequency energy source, an electrical energy source, or a laser energy source.

In some aspects, energizing the ceramic particles using energy from the energy sources can include energizing the ceramic particles by heat injection or a chemical reaction.

In some aspects, evaluating an effectiveness of the ceramic particles to recover heavy oil can include determining one or more of the energy sources applied to the ceramic particles that lead to a maximum quantity of the heavy oil recovered from the mixture.

In some aspects, a heavy oil recovery process is designed based on the evaluation.

The details of these and other aspects and implementations of the present disclosure are set forth in the accompa-

BRIEF DESCRIPTION OF THE DRAWINGS

Like reference numbers and designations in the various drawings indicate like elements.

DETAILED DESCRIPTION

Figure 1A:
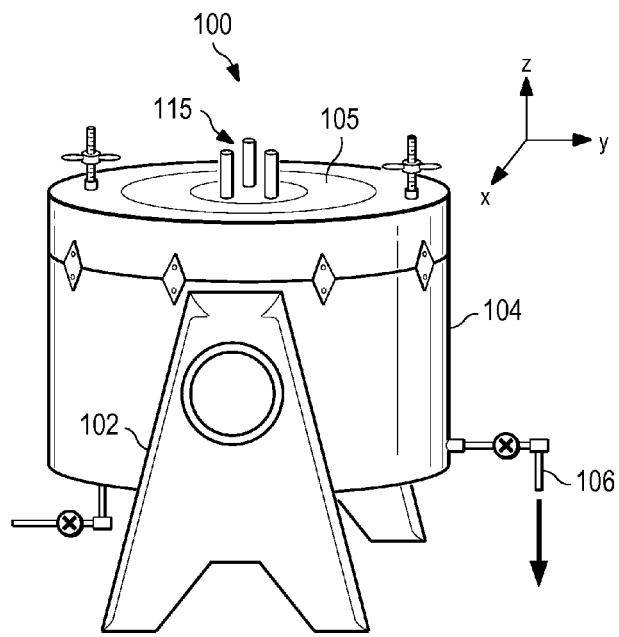
FIGS. 1A and 1B are schematic diagrams showing example vessel orientations of an example heavy oil recovery evaluation system.

This disclosure describes methods and systems for evaluating effectiveness of ceramic materials to recover hydrocarbons from a subterranean region. A subterranean region can include a formation, a portion of a formation or multiple formations. A subterranean region can contain hydrocarbons in its formation. Hydrocarbons can include oil, natural gas, and a mixture of them. Heavy hydrocarbon can include low American Petroleum Institute (API) gravity crude oil and tar. In some instances, heavy oil can be defined as API gravity <29 with viscosity more than 5000 Cp. Other definitions can be used. Techniques to evaluate the effectiveness of ceramic materials to recover hydrocarbons from a subterranean region is described with reference to recovering heavy oil. Similar techniques can be implemented to evaluate the ceramic materials ability to recover other hydrocarbons from the subterranean region.

To recover heavy oil from a subterranean region, a well bore can be formed in the subterranean region. Secondary recovery techniques such as thermal recovery methods can introduce heat into the subterranean region to increase temperature and lower viscosity of the heavy oil in the formation. As such, the mobility of the heavy oil can be enhanced and the heavy oil can flow into the well bore for production.

Example thermal recovery methods include steam injection (e.g., injecting heated steam into the formation), in-situ combustion (e.g., injecting an oxidizing gas (air or oxygen-enriched air) to generate heat by burning a portion of resident oil), in-situ steam generation, electric/electromagnetic heating, chemical reaction, and other techniques for introducing heat into the formation. For instance, in addition to steam, heated water, air, or any other fluid or gas carrying thermal energy can be injected into the formation. Electric, radio frequency (RF), microwave (MW), and laser energy can be used to heat water and generate steam beneath the surface for in-situ steam generation. Chemicals (e.g., exothermic reaction-components) can be injected into well bore such that the chemicals can react downhole and generate in-situ steam and/or other types of gas (e.g., nitrogen gas) to enhance heavy oil mobility.

In some implementations, ceramic materials can be injected into a subterranean region. The ceramic materials, when exposed to RF/MW/laser energy, can absorb the RF/MW/laser energy and be heated up rapidly reaching 1000° C. The ceramic materials can be molded and formed in any shape and size. For example, the ceramic materials can include ceramic particles, chunks of particles, etc. In some instances, water or other fluid can then be injected to the subterranean region for vaporization so that a large amount of steam can be generated beneath the surface.

In some implementations, the subterranean region can be fractured to create a fracture network. The ceramic particles can be used as proppants to be distributed throughout the fracture network. As such, the temperature distribution in the reservoir can be expanded to facilitate a wider range of heat penetration. The generated heat and steam can enhance flow and communications between the formations to the well bore for production, and enhance hydrocarbon recovery, especially heavy oil recovery in heavy oil and tar sand subterranean regions. Example techniques of using the ceramic materials for hydrocarbon recovery are described in U.S. patent application Ser. No. 14/147,914 and U.S. patent application Ser. No. 14/148,075 (both entitled "Electromagnetic Assisted Ceramic Materials for Heavy Oil Recovery and In-Situ Steam Generation" and filed on Jan. 6, 2014), which are incorporated herein by reference.

In some implementations, combining the ceramic material with the RF/MW/laser energy can expand the heat penetration into the hydrocarbon bearing formation and improve energy efficiency. Example system and method are disclosed to evaluate an effectiveness of the ceramic particles for in-situ steam generation and heavy oil recovery. The evaluation can be performed outside the well bore, for example, in a laboratory or another testing or experiment facility. The example system can be a laboratory test equipment for performing experiments and evaluation before field implementations of these techniques on site in a well system. For instance, experiments using different types of energy sources (e.g., RF/MW/laser energy source, electric heater, steam source, etc.) can be conducted to test, compare, and evaluate the effect of each energy source and combinations of the energy sources on the ceramic materials' ability to produce heat energy to convert water to steam. In some implementations, different heavy oil recovery techniques can be combined, for example, by using MW energy, RF energy, laser energy, heat injection, chemical reactions, or a combination thereof, to form a hybrid recovery approach to further improve heat penetration into the reservoir and heavy oil recovery. In some implementations, based on the evaluation results, a heavy oil recovery method (e.g., customized for a particular heavy oil and sand mixture of a particular formation) can be designed, tested, modified and eventually implemented (e.g., in a heavy oil formation).

In some implementations, the RF/MW/laser energy and ceramic material can heat up the surrounding wellbore to elevated temperature that can be used for condensate banking removal, blockages in the pore throat, allowing the fluid/condensate to flow or vaporize from the surrounding wellbore into the wellbore and removed.

In some implementations, the RF/MW/laser energy and ceramic material can heat up the surrounding wellbore to elevated temperature that can be used for clay treatment and wellbore stability. Some types of clays collapse at elevated temperature, for example, illite smectite mixed layer may collapse at 550° C.; the combination of ceramic materials and RF/MW/laser energy can be used for clay treatments.

In some implementations, the RF/MW/laser energy and ceramic material can heat up the surrounding wellbore to elevated temperature that can be used rock fracturing initiation. Elevated temperature caused by the combination of ceramic materials and RF/MW/laser energy can create fractures and microcracks around the wellbore, which can be used to apply hydraulic fracturing by pumping high pressure fluid through the initiated fractured caused by the RF/MW/laser energy.

Figure 1C:
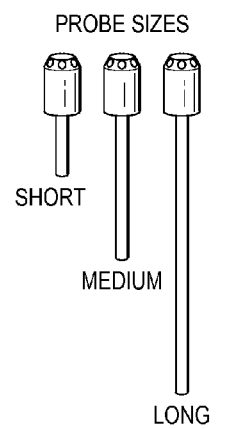
FIGS. 1C and 1D are schematic diagrams showing example probes of an example heavy oil recovery evaluation system.
Figure 1B:
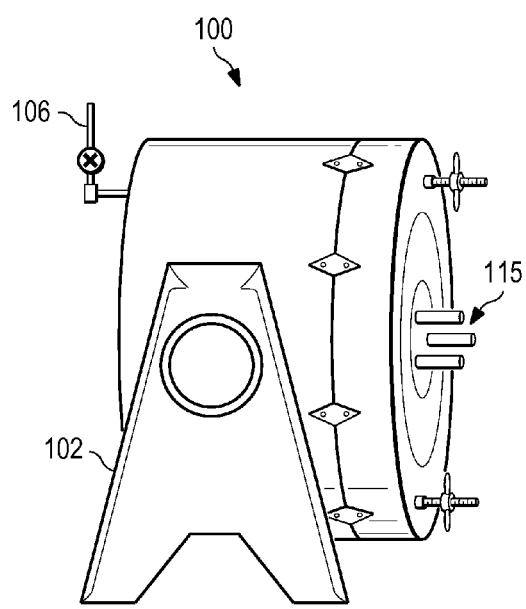

FIGS. 1A and 1B are schematic diagrams showing example vessel orientations of a heavy oil recovery evaluation system 100. The heavy oil recovery evaluation system 100 can include a base or a main holder 102 attached to a swivel cell 104. The swivel cell 104 is connected to a vessel 105 to swivel the vessel 105 from one orientation to another orientation. The vessel 105 can receive and contain a mixture of heavy oil and sand, for example, to simulate a particular subterranean region. The vessel 105 can further receive ceramic particles, water, steam, chemicals or other materials for simulating a heavy oil recovery process.

The vessel 105 includes ports to which one or more probes 115 can be connected to. The probes 115 can be used to transfer and deliver energy into the vessel 105, for example, to heat the ceramic particles. The heated ceramic particles can heat water, convert the water into steam. The generated steam can penetrate into the mixture to heat the heavy oil, thus improving the mobility and production of the heavy oil. In some implementations, the vessel 105 can include a top or cover to seal the vessel 105, for example, after the mixture and ceramic particles are placed into the vessel 105. The heavy oil recovery evaluation system 100 includes one or more drainages 106 (e.g., drainage production pipe), for example, to collect the produced heavy oil or any other surplus water, gas, or other materials injected (e.g., through the probes 115) into the vessel 105.

FIG. 1A shows an example vertical orientation of the vessel 105 while FIG. 1B shows an example horizontal orientation of the vessel 105. In general, the vessel 105 can be mounted at an arbitrary angle (e.g., from 0° to 90°) relative to the x, y, or z axis. In some implementations, the vertical orientation of the vessel 105 can be used to simulate a vertical well bore while the horizontal orientation of the vessel 105 can be used to simulate a horizontal well bore for oil recovery in a subterranean region. In some implementations, the orientation of the vessel 105 can be taken into account to analyze and evaluate, for example, the optimal vessel (or well bore) orientation of a particular oil recovery method for heavy oil recovery in a particular subterranean region (e.g., with a particular ratio of heavy oil to sand).

Figure 1D:
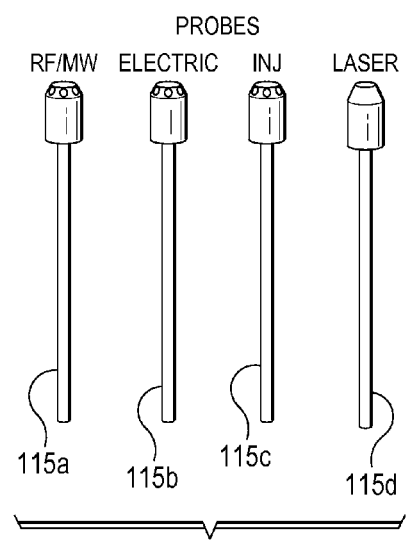

FIGS. 1C and 1D are diagrams showing example probes 115 that can be used with the example heavy oil recovery evaluation system 100. As shown in FIG. 1C, the probes 115 can have the same or different sizes (e.g., lengths, widths, etc.) and can be made of different materials. A shown in FIG. 1D, one or more of an RF/MW probe 115a, an electric probe 115b, an injection probe 115c, and a laser probe 115d (collectively referred to as probes 115) can be connected to the vessel 105. For instance, the injection probe 115c can be used to deliver one or more of steam, air, water, chemicals, or other materials into the vessel 105. In some implementations, the probes 115 can include antennas, waveguide, transmission line, or any other energy transfer media.

Figure 2:
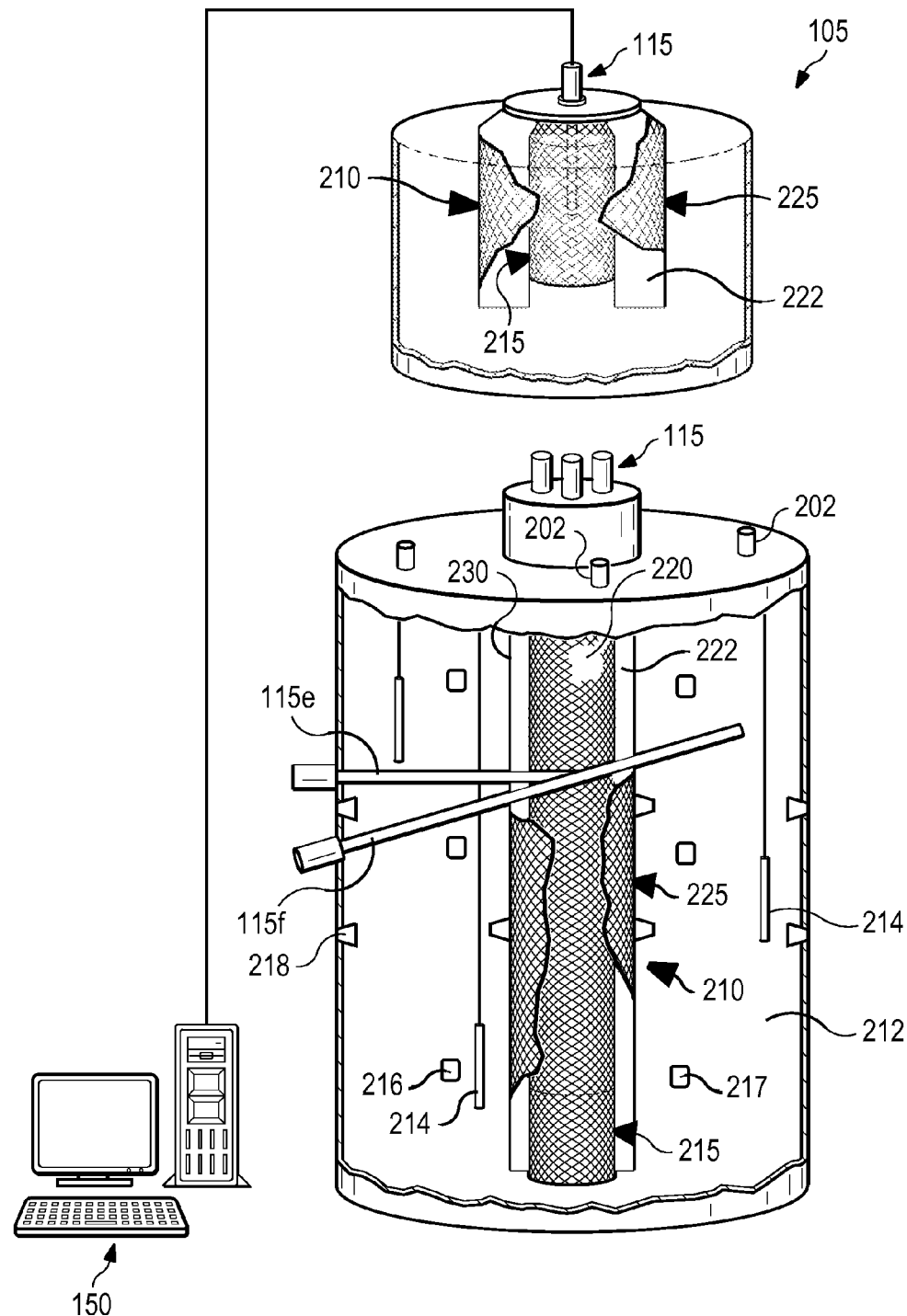
FIG. 2 is a schematic diagram showing a cross-sectional view of the vessel of the example heavy oil recovery evaluation system.
Figure 3:
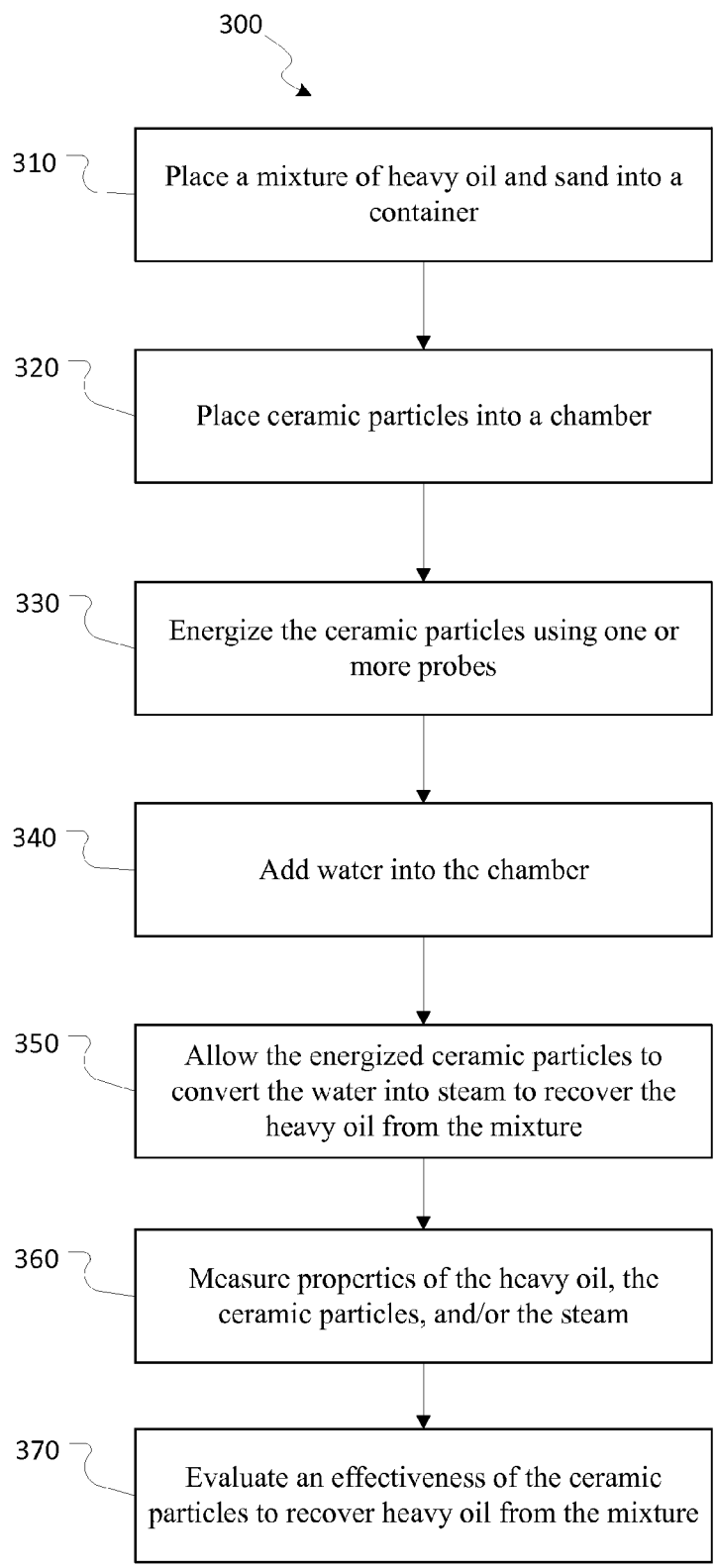
FIG. 3 is a flow chart of an example method for operating the example heavy oil recovery evaluation system.

FIG. 2 is a schematic diagram showing a cross-sectional view of the vessel 105 of the example heavy oil recovery evaluation system 100 of FIGS. 1A and 1B. FIG. 3 is a flow chart showing an example process 300 for operating the example heavy oil recovery evaluation system 100, for example, to evaluate effectiveness of ceramic materials to recover heavy oil.

The vessel 105 can be a container configured to receive a mixture 212 of heavy oil and sand. At 310, a mixture 212 of heavy oil and sand can be placed into the vessel 105. In some instances, the sand can include rock samples and/or sand packs of a particular formation or reservoir of interest. The heavy oil can include one or more types of heavy oil contained in the particular formation or reservoir, or other types of heavy oil that have the same or different viscosities. The mixture 212 of heavy oil and sand can have a particular oil-to-sand ratio, for example, to resemble the native oil-to-sand ratio of a particular formation or reservoir. Some example oil-to-sand ratios can be 50/50, 40/60, 30/70, 20/80, and 10/90.

In some implementations, the vessel 105 includes a chamber 210 configured to receive ceramic particles 222 and other materials (e.g., water, steam, gas, chemicals) that can be injected into the vessels (e.g., through an injection probe 115b). In the example shown in FIG. 2, the chamber 210 is implemented as a cylindrical bore extending axially inside the vessel 105. The chamber 210 can have another shape and located in another place within the vessel 105. In some implementations, the cylindrical bore can be regarded as a container positioned in chamber 210 to receive the ceramic particles 222, and other materials.

The chamber 210 includes a host/tool shield 215. The example host/tool shield 215 shown in FIG. 2 has a cylindrical shape and the inner surface of the host/tool shield 215 defines an inner bore 220. The inner bore 220 can configured to receive, for example, water, steam, gas, chemicals, or materials. The chamber 210 also includes a screen/liner 225. The host/tool shield 215 and screen/liner 225 forms a tubing 230 inside the chamber 210. The host/tool shield 215 expands the inner circumferential surface of the tubing 230 while the screen/liner 225 expands the outer circumferential surface of the tubing 230. The tubing 230 can be configured to receive the ceramic particles 222.

In some implementations, the host/tool shield 215 can help separate the water, steam, chemicals or other materials injected into the inner bore 220 from the ceramic particles 222 filled in the tubing 230. In some implementations, the tubing 230 can include a mesh that can protect these ceramic particles 222 from getting mixed with the sand in the mixture 212 contained in the vessel 105 and permit steam or other types of gas to pass through from the chamber 210 into mixture 212 in the vessel 105. In some instances, the mesh/host/tool shield 215 can be used to protect the probes 115, allow the probes 115 to transmit fluid, RF/MW, laser, or other materials and energy to the inner bore 220, and prevent sand and oil to invade the probes 115. The host/tool shield 215 can be made of stainless steel or any strong material that can resist rust. The screen/liner 225 can separate the ceramic particles 222 filled in the tubing 230 from the oil-sand mixture 222 contained in the vessel 105.

At 320, ceramic particles 222 can be placed into the chamber 210. For instance, the ceramic particles can be placed into the tubing 230 of the chamber 210. In some implementations, the tubing 230 of the chamber 210 can be implemented as a removable tubing that can be inserted into and/or removed from the chamber 210. The removable tubing can include the screen/liner 225 and the mesh/host/tool shield 215 as the inner and outer circumferential surfaces, respectively; or the removable tubing can be sized to fit into the slot defined by the screen/liner 225 and the mesh/host/tool shield 215. The removable tubing can be filled with ceramic particles. The ceramic particles can have different sizes and made of different materials. In some implementations, a removable tubing including a particular type of ceramic particles can be inserted into the chamber 210 in one experiment and can be replaced with another tubing including another type of the ceramic particles for another experiment.

The vessel 105 can be connected to one or more probes 115 that transfer energy from one or more energy sources, for example, to energize the ceramic particles 222. The probes 115 can extend longitudinally, radially, or at any angle relative to an axis of the vessel 105. As shown in FIG. 2, an axis of the vessel 105 is substantially vertical and a horizontal probe 115e and a tilted probe 115f can be inserted into the vessel 105. The probes 115 can be one or more of the probes 115a, 115b, 115c, and 115d described with reference to FIG. 1C, or other types of probes as appropriate. In some instances, the orientations of the probes 115 and/or the vessel 105 be critical for production and injection. For example, in some cases, if gravity is the main force for oil recovery, horizontal producers can be more suitable than vertical producers. In some implementations, the orientations of the probes 115 and/or the vessel 105 can be determined based on oil layers or oil 3D maps. For example, in some cases, if oil is located in vertical layers, a horizontal well can be appropriate because it can connect all these vertical layers for production. In some other cases, if oil exists in a huge matrix covering a large area, then a vertical well to inject heat can be more appropriate. The example heavy oil recovery evaluation system 100 allows evaluating different orientations of the probes 115 and/or the vessel 105 for determining the optimal configurations for oil recovery.

At 330, the ceramic particles 222 can be energized using one or more probes 115. In some implementations, an RF/MW probe can be inserted into the vessels (e.g., into the inner bore 220 or tubing 230). The ceramic particles 222 can absorb the RF/MW energy and convert them into heat energy. As such, the ceramic particles 222 can be heated to a high temperature within a short time. For example, the ceramic particles 222 can reach 1000° C. by being heated by an industrial microwave for 3 minutes.

At 340, water or other type of fluids can be added into the chamber 210 (e.g., the tubing 230 or other portions), for example, through one or more probes 115. At 350, when the water contacts the energized ceramic particles, the high temperature of the heated ceramic particles can convert the water into steam. The high temperature of the heated ceramic particles (e.g., around 1000° C.) helps generate high quality steam (e.g., steam with less water content), compared with lower temperature that may result in saturated steam (e.g., steam with greater water content than high quality steam). For example, the steam quality at 400° F. can be better than that at 350° F. At an even higher temperature like 800° F., dry steam with high latent heat can be obtained. The high temperature of the heated ceramic particles also helps produce a larger amount of steam within a shorter time period.

The large volume of high quality steam can be used as the main drive to recover oil. For example, the steam can pass through the mesh or screen/liner 225 of the chamber 210 and flow into the vessel 105 that is filled with the mixture 212 of heavy oil and sand. The steam can raise the temperature of the mixture 212, reduce viscosity of the heavy oil, and increase heavy oil mobility to allow the oil to drain and flow, for example, downward to produce via a drainage production pipe (e.g., the drainage production pipe 106 in FIGS. 1A and 1B). In some implementations, the vessel 105 can include one or more vents 202, for example, to vent surplus steam or gas.

In some implementations, the chamber 210 can be used to simulate a well bore in a subterranean region while the vessel 105 filled with the heavy oil and sand mixture 212 can be used to simulate the surrounding subterranean region of the well bore. In some implementations, the ceramic particles 222 can be used as proppants to be distributed in fractures in the subterranean region. To evaluate the effectiveness of the ceramic particles as proppants, in some implementations, the chamber 210 can be configured to include multiple branches (not shown) to simulate the fractures. The multiple branches can be filled with the ceramic particles 222, extending (e.g., radially from the chamber 210) into the mixture 212 of heavy oil and sand in the vessel 105 (e.g., with or without a screen/liner). As the heated ceramic particles 222 can be distributed in the tubing 230 and the branches, water can be heated multiple times as it pass through the heated ceramic particles 222 from location to location. Accordingly, more steam can be generated and the quality of the steam can be improved by reheating it and converting to dry high quality steam.

To evaluate the effectiveness of the ceramic particles 222 for steam generation and heavy oil recovery, the heavy oil recovery evaluation system 100 includes various sensors to monitor the conditions and properties of the various components of the heavy oil recovery evaluation system 100. For example, the sensors can quantitatively measure properties of one or more of the heavy oil, the ceramic particles, the steam or other parameters associated with the example heavy oil recovery evaluation system 100. Evaluation can then be performed based on the measured properties.

The sensors can include temperature sensors 214 (e.g., thermometers or thermocouples), acoustic sensors 216, fluid sensors (e.g., viscometers) 217, pressure sensors/strain gages 218, or other types of measurement equipment. For example, one or more temperature sensors 214 can be used to measure the temperature of the ceramic particles, the steam, and the heavy oil before, during, and after a recovery or evaluation process. The acoustic sensors 216 can be used to measure, for example, oil flow, strength of the rock, any sand production, wellbore stability, and change in rocks compaction. The fluid sensors can be used to measure the viscosity and/or velocity of the heavy oil or other fluids in the example heavy oil recovery evaluation system 100. The pressure sensors/strain gages 218 can be used to measure the pressure at different portions of the example heavy oil recovery evaluation system 100.

The sensors can be located at various positions in the heavy oil recovery evaluation system 100. For example, the sensors can be installed within the vessel 105 and distributed in the mixture 212 of heavy oil and gas, within the inner bore 220, tubing 230, or any other locations. In some implementations, the same type of sensors can be placed at different locations to measure the properties of the steam, ceramic particles, and the mixture of heavy oil and sand, for example, to evaluate the heat penetration and viscosity change of the heavy oil across space and/or time.

In some implementations, in addition to or as an alternative to the RF/WF energy, the ceramic particles can be heated by electric, laser, or other energies delivered by respective probes. For instance, chemicals (e.g., exothermic reaction-components) can be injected into the inner bore 220 of the chamber 210 where the chemical reacts and generate heat and other products (e.g., in-situ steam and nitrogen gas). As a specific example, ammonium chloride and sodium nitrite can be injected using two different probes into the chamber 210 (e.g., the inner bore 220) simultaneously. An acid (acetic acid) can be injected using a third probe to activate the reaction. In some implementations, the reaction can also be activated using MW or electric heating. The required temperature to activate the reaction is 50 to 90° C., depending on the initial pressure of the chamber 210. The injected chemicals can react, for example, according to:

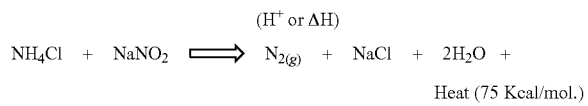

$$NH_4Cl + NaNO_2 \xrightarrow{(H^+ \text{ or } \Delta H)} N_{2(g)} + NaCl + 2H_2O + \text{Heat (75 Kcal/mol.)}$$

The products of the reaction can include heat (e.g., 225 Kcal/L mixtures) and $N_2$ gas (e.g., around 60 L/L mixture). The generated heat can increase the temperature of the ceramic particles 222 and the generated steam and gas can be allowed to pass through the chamber 210 into the vessel 105 to recover the heavy oil from the mixture 212.

At 360, properties of one or more of the heavy oil, the plurality of ceramic particles, the steam, or the energy sources can be measured. For example, the sensors (e.g., sensors 214, 216, 217, and 218) of the example heavy oil recovery evaluation system 100 can measure and collect the measurement data. Example measurement data can include, for example, the temperature of the ceramic particles, the steam, and/or the heavy oil, a pressure of the steam, a pressure inside the inner bore 220 (e.g., where the chemical reactions can occur), the tubing 230, and the vessel 105, and viscosities and/or velocities of the heavy oil (e.g., before and after the steam generation and/or production), the volume and quantity of the produced heavy oil. In some implementations, the properties (e.g., the frequency, power level, energy consumption, etc.) of the different energy sources can be measured. Additional or different properties (e.g., the amount of time it takes to produce the heavy oil, the amount of steam it required to produce heavy oil, etc.) can be measured. The various properties can be measured continuously, periodically, from time to time, or per request.

Based on the measurement data, the effectiveness of the ceramic particles 222 to recover heavy oil from the mixture 212 can be evaluated, for example, by a computer system. The example heavy oil recovery evaluation system 100 includes a computer system 150 to obtain and analyze the measurement data. The computer system 150 or any of its components can be coupled to the vessel 105, for example, via one or more wirelines or wireless connections. The computer system 150 can be located near the vessel 105, remotely from the vessel 105 (e.g., via wireless communications links), or at any suitable location. For example, the computer system 150 can be located at a data processing center, a computing facility, or another suitable location.

The computer system 150 can include one or more data processing apparatus (e.g., one or more processors), a computer-readable medium (e.g., a memory, a random access memory (RAM), a writable read-only memory (ROM), a hard disk, etc.), and input/output device. The input/output devices can include display device, input devices (e.g., keyboard, mouse, etc.), and/or other input/output devices). The computer system 150 can be connected to a network. For example, the network can include a wireless and/or a wired network, a Local Area Network (LAN), a Wide Area Network (WAN), a private network, a public network (such as the Internet), a WiFi network, a network that includes a satellite link, and/or another type of data communication network. At 370, an effectiveness of the ceramic particles to recover heavy oil from the mixture can be evaluated. For example, the computer system 150 can receive measurement data collected by the sensors (e.g., sensors 214, 216, 217, and 218), and evaluate the effectiveness of the ceramic particles based on the measurement data. In general, the computer system 150 can evaluate the effectiveness of the ceramic particles based on the measurement data over time and space. For instance, the measurement data can be processed and presented in a table, a plot, a graph, or a combination of these and other formats against time to show a trend of, for example, heat penetration, flow of the steam, and the flow of the heavy oil. In some implementations, the computer system 150 can identify the locations of the sensors in the vessel 105 and evaluate the measured data against the locations to determine, for example, the direction, speed, and depth of heat penetration. In some implementations, the computer system 150 can identify the orientation of the vessel 105 (e.g., vertical or horizontal as shown in FIGS. 1A and 1B, or any other orientation), identify the orientation of the one or more probes 115 relative to the vessel 105 (e.g., vertically oriented probes or horizontally oriented probes 115e and 115f); and analyze their effects on steam generation and oil production. For example, optimal vessel orientation and probe orientations can be determined, for example, based on quantities of the recovered heavy oil. In some instances, an optimal well bore orientation for a field implementation of a heavy oil recovery process can be determined optimal vessel orientation and probe orientations.

In some implementations, the computer system 150 can evaluate the effects of the temperatures of ceramic particles on the generation speed, quality, and quantity of the steam. The computer system 150 can evaluate the effects of the temperature, quality, and quantity of the steam on the viscosity, velocity and production of the heavy oil. The computer system 150 can monitor the pressures in various portions inside the vessel, analyze their effects on, for example, chemical reactions, heat penetration, and viscosity change of the heavy oil.

In some implementations, the computer system 150 can evaluate the effects of the ceramic particles (e.g., the shape, size, and number), frequency of the RF/WF, power of the energy sources, heating time, or other factors on the steam generation and oil production. For instance, these factors can be changed during a single test/experiment or different values of these factors be applied in multiple tests/experiments (e.g., according to the example process 300) to obtain measurement data. In some implementations, based on the measurement data, the computer system 150 can determine optimal values of these factors and can, for example, control the volume and quantity of the generated steam based on the determination. In some implementations, the volume and quantity of the generated steam can be customized or otherwise controlled, for example, based on a particular mixture of heavy oil and sand of a subterranean region, the properties of the heavy oil, or other factors. In some implementations, the volume and quantity of the generated steam can be controlled to achieve the optimize oil to steam ratio (OSR) (e.g., 0.2, every 10 barrel of steam can produce 2 barrel of oil).

In some implementations, evaluating the effectiveness of the ceramic particles to recover heavy oil from the mixture include determining an optimal recovery techniques for a particular heavy oil or a mixture of heavy oil and sand. For example, different oil recovery techniques (e.g., with energy sources and combinations of them) can be tested/experimented (e.g., according to the example process 300) to energize the ceramic particles to recover the heavy oil from the mixture. The computer system 150 can collect, compare, or otherwise analyze the different test/experiment results to determine the optimal recovery technique (e.g., based on a certain criterion). For example, the computer system 150 can compare or otherwise analyze properties (e.g., quantities and qualities) of the produced heavy oil, the production speeds, the amounts of consumed energies, or other attributes of the different oil recovery techniques to determine, for example, which energy or which combination of energies are the most efficient to recover the particular heavy oil. For example, the computer system 150 can determine one or more of the energy sources that can be applied to the ceramic particles that lead to a maximum quantity of the heavy oil recovered from the mixture.

In some implementations, the evaluated results can be output, for example, in text, table, graph, chart, or other format through one or more output devices (e.g., a graphic user interface on a display) to a user. In some implementations, a heavy oil recovery process can be designed, tested, modified or controlled based on the evaluations, for example, to incorporate the optimal energy source, heating time, and well bore orientation suitable for a targeted heavy oil and sand in a targeted subterranean region.

While this disclosure contains many specific implementation details, these should not be construed as limitations on the scope of any implementations or of what may be claimed, but rather as descriptions of features specific to particular implementations of particular implementations. Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

The invention claimed is:

1. A heavy oil recovery evaluation system comprising:
a vessel configured to contain a mixture of heavy oil and sand, the vessel including a chamber to receive a plurality of ceramic particles and water;
a plurality of probes inserted to the vessel to transfer energy from a plurality of energy sources for energizing the plurality of ceramic particles, wherein the energized ceramic particles convert the water into steam to recover the heavy oil from the mixture;
a swivel connected to the vessel, the swivel configured to swivel and orient the vessel at a plurality of orientations, wherein the plurality of orientations comprise at least a horizontal orientation and a vertical orientation; and
a computer system connected to the vessel to evaluate an effectiveness of the plurality of ceramic particles to recover heavy oil from the mixture.

2. The system of claim 1, wherein the plurality of probes are configured to transfer two or more of microwave energy, radio frequency energy, electrical energy, or laser energy to heat the plurality of ceramic particles.

3. The system of claim 1, wherein the vessel is a first vessel, and wherein the system further comprises a second vessel positioned in the chamber, wherein the plurality of ceramic particles and the water are received in the second vessel.

4. The system of claim 3, wherein the second vessel comprises a mesh to permit the steam to pass through.

5. The system of claim 1, further comprising a plurality of sensors connected to the computer system to measure properties of one or more of the heavy oil, the plurality of ceramic particles, or the steam.

6. The system of claim 5, wherein the plurality of sensors comprise a temperature sensor to measure a temperature of the steam and a pressure sensor to measure a pressure of the steam.

7. The system of claim 5, wherein the plurality of sensors comprise a viscometer to measure a viscosity of the heavy oil.

8. The system of claim 5, wherein, to evaluate an effectiveness of the plurality of ceramic particles to recover heavy oil from the mixture, the computer system is configured to:
obtain the measured properties of the one or more of the heavy oil, the plurality of ceramic particles, or the steam; and
evaluate the effectiveness of the plurality of ceramic particles to recover heavy oil from the mixture based on the measured properties.

9. The system of claim 1, wherein the swivel is configured to orient the vessel at the horizontal orientation, and at least one of the plurality of probes is inserted into the vessel horizontally.

10. The system of claim 1, wherein the swivel is configured to orient the vessel at the vertical orientation, at least one of the plurality of probes is inserted into the vessel vertically, and at least another one of the plurality of the probes is inserted into the vessel horizontally.

11. The system of claim 1, wherein the plurality of probes are inserted through an upper surface of the vessel, and the plurality of probes have different lengths and reach different depths in an inner volume of the vessel.

12. A method comprising:
placing a mixture of heavy oil and sand into a vessel, said vessel including a chamber and a swivel connected to the vessel, the swivel configured to swivel and orient the vessel at a plurality of orientations, wherein the plurality of orientations comprise at least a horizontal and a vertical orientation;
placing a plurality of ceramic particles into the chamber;
inserting a plurality of probes into a corresponding plurality of ports formed in an outer surface of the vessel to transfer energy from a plurality of energy sources for energizing the plurality of ceramic particles;
energizing the plurality of ceramic particles using the plurality of probes connected to the vessel;

adding water into the chamber;

allowing the energized ceramic particles to convert the water into steam to recover the heavy oil from the mixture; and evaluating an effectiveness of the plurality of ceramic particles to recover heavy oil from the mixture.

13. The method of claim 12, wherein energizing the plurality of ceramic particles using the plurality of probes inserted into the vessel comprises heating the plurality of ceramic particles using the plurality of probes transferring two or more of microwave energy, radio frequency energy, electrical energy, or laser energy.

14. The method of claim 12, further comprising measuring properties of one or more of the heavy oil, the plurality of ceramic particles, or the steam.

15. The method of claim 14, wherein evaluating an effectiveness of the plurality of ceramic particles to recover heavy oil from the mixture comprises:

obtaining the measured properties of the one or more of the heavy oil, the plurality of ceramic particles, or the steam; and evaluating the effectiveness of the plurality of ceramic particles to recover heavy oil from the mixture based on the measured properties.

16. The method of claim 12, further comprising:
collecting the recovered heavy oil; and
measuring a property of the recovered heavy oil.

17. A method comprising:

energizing, using energy from a plurality of energy sources through a plurality of probes inserted into a laboratory heavy oil recovery evaluation system vessel, a plurality of ceramic particles positioned in a chamber in the laboratory heavy oil recovery evaluation system vessel, the chamber comprising a mixture of heavy oil and sand;

recovering heavy oil from the mixture using steam formed by flowing water over the energized plurality of ceramic particles;

measuring a property of the heavy oil recovered from the mixture; and evaluating an effectiveness of the plurality of ceramic particles to recover heavy oil from a subterranean region based, at least in part, on the property of the heavy oil recovered from the mixture;

wherein a swivel is connected to the laboratory heavy oil recovery evaluation system vessel, the swivel configured to swivel and orient the vessel at a plurality of orientations, the plurality of orientations comprising at least a horizontal and a vertical orientation.

18. The method of claim 17, wherein the plurality of energy sources comprises two or more of a microwave energy source, a radio frequency energy source, an electrical energy source, or a laser energy source.

19. The method of claim 17, wherein energizing, using energy from a plurality of energy sources, a plurality of ceramic particles comprises energizing the plurality of ceramic particles by heat injection or a chemical reaction.

20. The method of claim 17, wherein evaluating an effectiveness of the plurality of ceramic particles to recover heavy oil from a subterranean region based, at least in part, on a property of the heavy oil recovered from the mixture comprises determining one or more of the plurality of energy sources applied to the plurality of ceramic particles that lead to a maximum quantity of the heavy oil recovered from the mixture.

21. The method of claim 17, further comprising designing a heavy oil recovery process based on the evaluation.

22. The method of claim 17, further comprising measuring a property of the plurality of ceramic particles; and wherein evaluating the effectiveness of the plurality of ceramic particles to recover heavy oil from the subterranean region based, at least in part, on the property of the heavy oil recovered from the mixture comprises evaluating the effectiveness of the plurality of ceramic particles to recover heavy oil from the subterranean region based, at least in part, on the property of the heavy oil recovered from the mixture and the property of the plurality of ceramic particles.

23. The method of claim 22, wherein measuring a property of the plurality of ceramic particles comprises measuring one or more of a shape, size, material, and number of the plurality of ceramic particles; and wherein evaluating the effectiveness of the plurality of ceramic particles to recover heavy oil from the subterranean region based, at least in part, on the property of the heavy oil recovered from the mixture and the property of the plurality of ceramic particles and the property of the plurality of ceramic particles comprises evaluating an effect of the one or more of the shape, size, material, and number of the plurality of ceramic particles on steam generation and oil production to recover heavy oil from the subterranean region.

24. The method of claim 17, wherein evaluating the effectiveness of the plurality of ceramic particles to recover heavy oil from the subterranean region based, at least in part, on the property of the heavy oil recovered from the mixture comprises evaluating effects of temperatures of ceramic particles on one or more of a generation speed, quality, and quantity of the steam formed by flowing water over the energized plurality of ceramic particles.

25. The method of claim 17, further comprising:

orienting the vessel at one of the plurality of orientations;

orienting the plurality of probes at respective plurality of orientations relative to the one of the plurality of orientations of the vessel;

wherein recovering heavy oil from the mixture comprises recovering the heavy oil from the mixture using the vessel oriented at the one of the plurality of orientations and the plurality of probes oriented at the respective plurality of orientations relative to the one of the plurality of orientations of the vessel; and determining an optimized orientation, out of the plurality of orientations, of the vessel and optimized respective orientations, out of the respective plurality of orientations relative to the one of the plurality of orientations of the vessel, of the plurality of probes based on a quantity of the heavy oil recovered from the mixture resulting from using the vessel oriented at the one of the plurality of orientations and the plurality of probes oriented at the respective plurality of orientations relative to the one of the plurality of orientations of the vessel.

26. The method of claim 25, further comprising determining a well bore orientation for a field implementation of a heavy oil recovery process based on the optimized orientation of the vessel and the respective optimized orientations of the plurality of probes.

* * * * *